United States Patent [19]

Ogren et al.

[11] Patent Number: 4,689,052

[45] Date of Patent: Aug. 25, 1987

[54] VIRTUAL IMPACTOR

[75] Inventors: John A. Ogren, Hagersten; Jost Heinzenberg, Sollentuna, both of Sweden; Robert L. Charlson, Seattle, Wash.

[73] Assignee: Washington Research Foundation, Seattle, Wash.

[21] Appl. No.: 830,966

[22] Filed: Feb. 19, 1986

[51] Int. Cl.$^4$ ............................................. B01D 45/04
[52] U.S. Cl. .......................................... 55/17; 55/261; 55/266; 55/267; 55/270; 55/338; 73/863.12; 73/863.23
[58] Field of Search ................... 55/270, 17, 1, 80, 97, 55/261, 266, 267, 315, 338, 468; 73/863.12, 863.23, 864.34, 28, 29

[56] References Cited

U.S. PATENT DOCUMENTS

| | | | |
|---|---|---|---|
| 2,550,933 | 5/1951 | McEvoy | 55/270 X |
| 3,011,336 | 12/1961 | Weiss | 73/863.12 |
| 3,193,991 | 7/1965 | Browning et al. | 55/338 X |
| 3,199,270 | 8/1965 | Oehlrich | 55/261 |
| 3,252,323 | 5/1966 | Torgeson | 73/28 X |
| 3,315,806 | 4/1967 | Sigwart et al. | 55/261 X |
| 3,938,390 | 2/1976 | Grey | 55/270 X |
| 4,004,882 | 1/1977 | Byrne et al. | 73/863.12 X |
| 4,060,001 | 11/1977 | Archerd | 73/864.34 X |
| 4,154,088 | 5/1979 | Werner | 73/28 |
| 4,191,541 | 3/1980 | Jenkins | 55/270 X |

FOREIGN PATENT DOCUMENTS

1445061 8/1976 United Kingdom ................ 55/338

*Primary Examiner*—Kathleen J. Prunner
*Attorney, Agent, or Firm*—Christensen, O'Connor, Johnson & Kindness

[57] ABSTRACT

Disclosed is a virtual impactor for separating particles of a predetermined size range from an aerosol, and for transporting the separated particles from the region they are separated from the aerosol to an analysis/collection region remote therefrom. The device comprises a conduit member having an inlet end and an outlet end. The conduit member is configured to define a substantially enclosed passageway between the inlet end and the outlet end. At least a portion of the conduit member is gas-permeable. The outlet end of the conduit member is positioned adjacent to the analysis/collection region. The virtual impactor is moved relative to the aerosol to be sampled (or the aerosol is moved relative to the impactor). The virtual impactor utilizes an operating gas that is introduced into the impactor through the gas-permeable portion of the conduit member. The operating gas is then bifurcated into a counterflow fraction that exits the inlet end of the conduit member, and a transporting flow fraction that passes along the conduit member to the analysis/collection region. The counterflow fraction is readily adjustable to control the size of the particles entering the analysis/collection region. Since the operating gas is introduced into the conduit member through the permeable portion of that member, separated particles transported therein are prevented from colliding with the inner surface of the conduit member and are thus not lost or contaminated.

16 Claims, 5 Drawing Figures

VIRTUAL IMPACTOR

TECHNICAL FIELD

This invention pertains to virtual impactors for separating particles from an aerosol for analysis.

BACKGROUND INFORMATION

Aerosols are a suspension of solid or liquid particles in a gas. Aerosols that include particles with diameters of 1 micrometer or larger can be characterized as coarse-particle aerosols. The particles in coarse-particle aerosols can be composed of mechanically produced solid particles, mechanically produced spray droplets, or atmospheric cloud droplets.

To most effectively study the physical and chemical characteristics of the aerosol particles, it is necessary to separate the particles from the aerosol gas and transport the separated particles to a point where they can be either collected for later study or scrutinized in situ with suitable analytical instruments. Often it is desirable to sample and study only a particle size or range of sizes of particles. For accurate sampling and analysis, it is also important that the particles to be sampled are effectively separated, i.e., isolated from other aerosol particles having sizes outside of the desired range. Furthermore, the separated particles must be transported to the region where they are collected or analyzed without colliding with the structure of the sampling device. Such collisions result in losses when the particles adhere to the structure. Even if the particles collide but bounce off the structure they may be contaminated through contact with the structure.

In the past, devices known as impactors have been used for separating particles from the aerosol gas. Generally, impactors consist of an impaction plate and means for causing the aerosol to flow toward the plate. The direction of the aerosol flow is abruptly changed near the impaction plate so that the particles with sufficient inertia will deviate from the flow where it changes direction and impact upon the plate. The particles that collect on the plate are subsequently collected and/or analyzed.

The determination of which particles will deviate from the flow and impact upon the plate depends essentially upon two parameters. These parameters are: the particle's inertia, as quantified by a parameter known as the "stop distance" L; and the minimum radius of curvature $r_c$ of the streamlines of the aerosol gas flow in the region where the flow changes direction. The streamlines are lines in the gas flow of the aerosol which are everywhere parallel to the direction of flow at a given instant. For spherical particles having a diameter of 1 micrometer or larger, the stop distance L is defined as follows:

$$L = V_i m B f$$

where $V_i$ = the impaction velocity, defined as the velocity of the particle at a distance upstream from the directional change of the aerosol flow.

m = the mass of the particle.

B = the mobility of the particle, defined as the particle velocity per unit of drag force under steady state conditions. In equation form:

$$B = 1/(6\pi\eta r_p)$$

where n = viscosity of the aerosol gas.

$r_p$ = particle radius.

and f = a correction factor for particles with upstream Reynolds numbers, $Re_i$, greater than unity, in equation form:

$$f = 3\epsilon^{-3/2} Re_i^{-1}[Re_i^{\frac{1}{3}}\epsilon^{\frac{1}{2}} + \arctan(Re_i^{-\frac{1}{3}}\epsilon^{-\frac{1}{2}}) - \pi/2.$$

where $Re_i = 2 r_p \rho V_i/\eta$.

$\rho$ = density of the gas.

$\epsilon \cong 1/6$, a numerical constant.

It is known that when the ratio of the stop distance L to the radius of curvature $r_c$ is much greater than unity for a particle, that particle will deviate from the streamlines of the gas flow and impact upon an object if one is present. The ratio of the stop distance L to the radius of curvature $r_c$ of the gas flow streamline is referred to as the Stokes number, Stk. Therefore, in order to separate particles of a known stop distance from a passing flow of the aerosol, the structure must be arranged so that the radius of curvature $r_c$ of the streamlines of the aerosol flow is small enough near the impaction plate to create a Stokes number of greater than 1 for that particular particle.

One problem with conventional impactors is that the separated particles have a tendency to bounce off the impaction plate and become reentrained within the flow. Furthermore, conventional impactors are designed to accumulate particles on the impaction plate prior to analysis. For some particles, such as cloud droplets, this accumulation makes accurate analysis of certain characteristics of these particles extremely difficult. More particularly, cloud droplets are typically comprised of a volatile solvent such as water containing various solutes such as sulfuric acid, nitric acid, bisulfate compounds and others. Once the cloud droplets are separated and impact upon the impaction plate, the liquid solvent undergoes mixing and, usually, uncontrolled evaporation. Furthermore, the properties of the solutes (some of which, such as nitric acid, are volatile themselves) undergo rapid changes, thereby making it practically impossible to capture and measure these solutes with conventional impactors. Nonvolatile solutes may also undergo physical or chemical changes due to contamination through contact with the impaction plate and/or other stolutes accumulated on that plate.

Some impaction devices, known as virtual impactors, are configured to avoid the problem of particles bouncing off the impaction plate and becoming reentrained in the aerosol flow. These devices are known as virtual impactors because there is no particle impaction with a solid object at the point where particles separate from the flow. Rather, the separated particles are directed from the point of separation to a collection region located away from the remainder of the aerosol flow. For example, in one type of virtual impactor such as that shown in U.S. Pat. No. 4,301,002, issued to Loo, the aerosol flow is directed from a nozzle toward a spaced-apart hollow collection probe. Suction is applied across the space between the nozzle and the probe in order to divert a portion of the aerosol flow away from the probe. The diverted portion of the flow carries most of the small-inertia particles from the probe. The remaining undiverted portion of the original aerosol flow (hereinafter "sampling flow") is directed into the collection probe. The larger particles (the precise size of which depends upon the magnitude of the applied suction) separate from the diverted flow and are carried by the sampling flow into the collection probe where they are collected on a filter located away from the flow diversion region.

Past virtual impactor designs may reduce the particle reentraining problem discussed with respect to conventional impactors, but since the sampling flow is merely an undiverted portion of the original aerosol flow, the collected particles will necessarily include some small-inertia particles in the same concentration as in the general aerosol. As noted, unseparated small-inertia particles will adversely affect the accuracy of coarse particle analysis. Past virtual impactors also lack provisions for minimizing losses or contamination due to particle collisions with the walls of the probe or conduit in which the separated particles flow. Furthermore, these devices propose no effective means of transporting and treating separated liquid droplets so that the solvent and solute of that droplet can be accurately analyzed in situ.

SUMMARY OF THE INVENTION

This invention is directed to a virtual impactor that includes the utilization of an operating gas for effective, easily controlled separation of particles from an aerosol. Once separated, the particles are transported to a remote region for in situ analysis or collection. The operating gas is controlled to effect minimal collision losses or contamination of the transported particles within the structure of the impactor. Furthermore, since all of the aerosol gas is diverted from the analysis/collection region, the above-noted problem of some unseparated small-inertia particles reaching that region is solved by this invention.

As another aspect of this invention, when cloud droplets are separated for analysis, the operating gas is heated in order to evaporate the liquid of the cloud droplets within the confines of the impactor. The water vapor produced is readily measured with a hygrometer. Other fractions of the evaporated liquid droplet (e.g., gaseous or solid particle solutes) can be analyzed within the confines of the device through the use of suitable analytical instruments.

A virtual impactor formed in accordance with this invention particularly comprises a conduit member having an inlet end and an outlet end and defining a substantially enclosed passageway between the inlet and outlet ends. At least a portion of the conduit member is gas-permeable. By either moving the device through the aerosol or forcing the aerosol past the device, a portion of the aerosol particles are directed into the inlet end of the conduit member. Impactor operating gas is forced through the permeable portion of the conduit member into the passageway. The flow of the operating gas is controlled so that one fraction of the gas exits the passageway through the inlet end of the conduit member, and the remaining fraction of the operating gas is drawn through the passageway to the outlet end of the conduit member. The fraction of the gas that is directed to the outlet end of the conduit member transports the relatively large-inertia particles to a region where they are analyzed and/or collected. The fraction of the operating gas that exits the inlet end of the conduit member prevents small-inertia particles from reaching the collection/analysis region. The size of the particles permitted to pass into the transporting fraction of the operating gas is readily controlled by adjusting the relative flow rates of the impactor operating gas flow fractions. The introduction of the operating gas through the permeable conduit member creates a radially inward flow of gas near the inner surface of the conduit member that tends to prevent the collision of separated particles against that surface.

DETAILED DESCRIPTION OF THE INVENTION

Figures 1, 5:
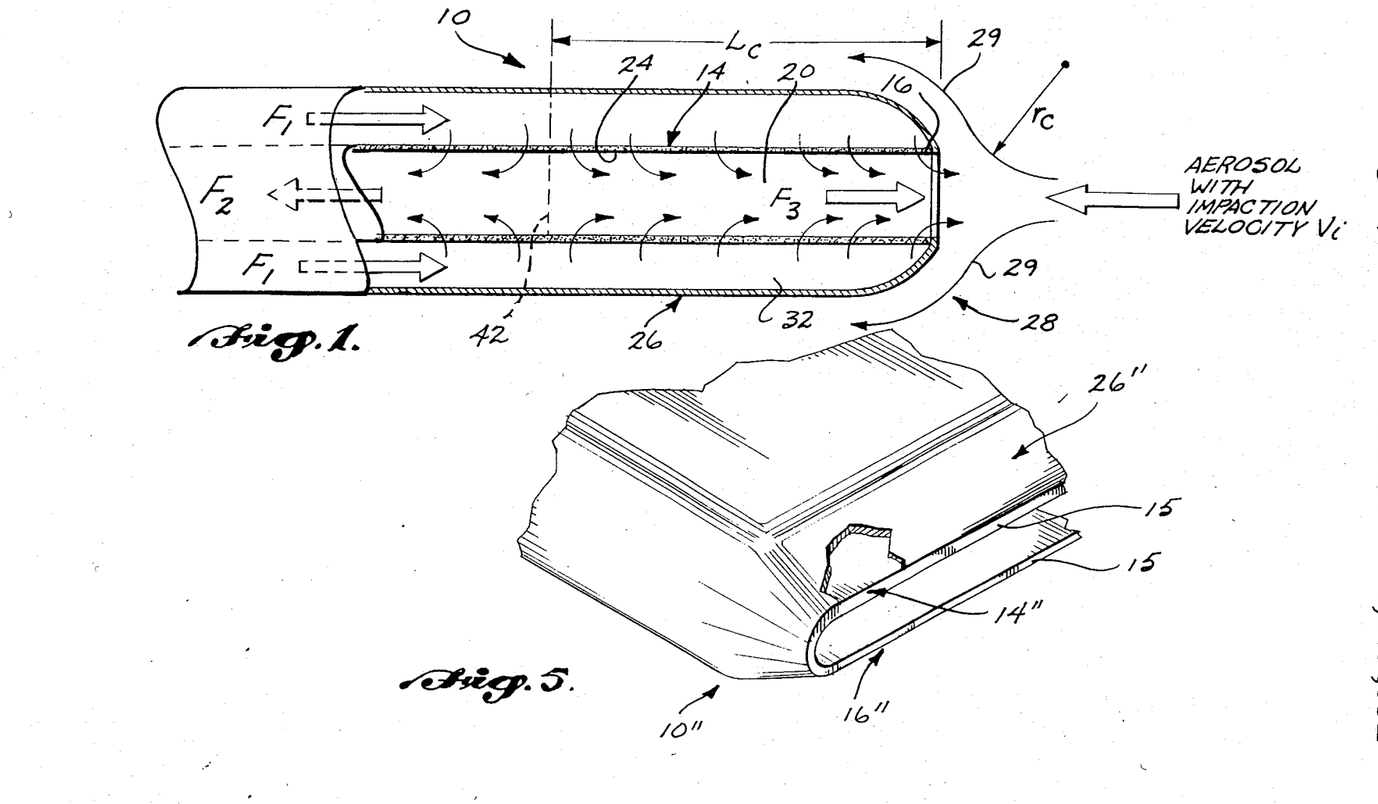
FIG. 1 is a schematic cross-sectional view of a virtual impactor formed in accordance with this invention.
FIG. 5 is an alternative embodiment of a virtual impactor formed in accordance with this invention.
Figure 2:
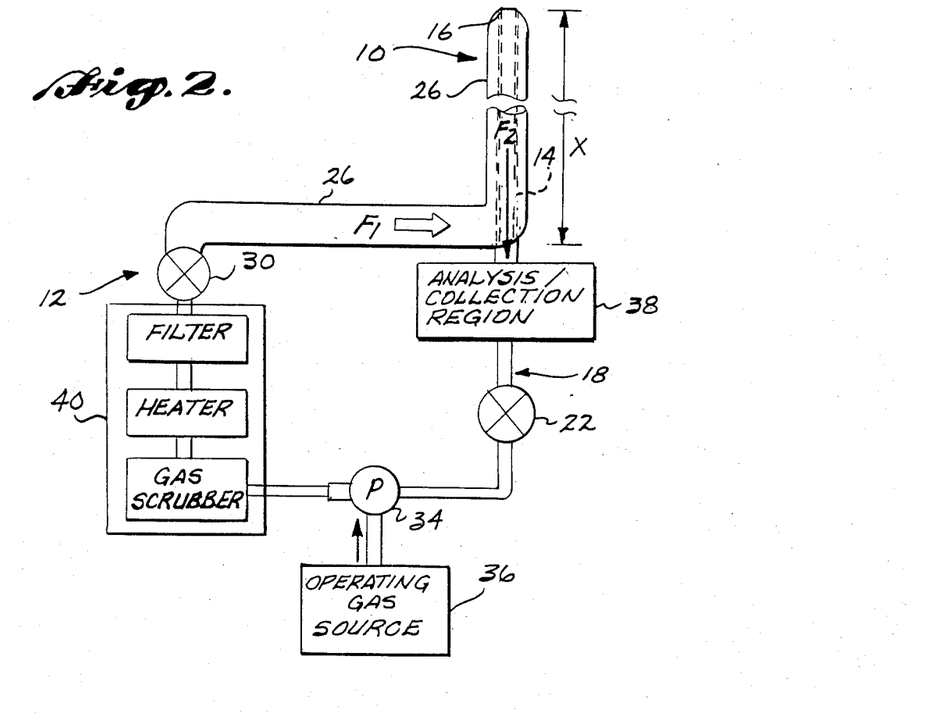
FIG. 2 is a diagram of one embodiment of a flow system usable with the virtual impactor of FIG. 1.

FIGS. 1 and 2 respectively show a schematic cross-sectional view of a preferred embodiment of a virtual impactor 10 formed in accordance with this invention and a preferred flow system 12 for controlling its operation. The depicted device is adaptable for any type of ground-based or atmospheric aerosol sampling. For atmospheric aerosol sampling, the device can be mounted to an aircraft and flown through the aerosol (e.g., clouds).

The virtual impactor 10 comprises a tubular conduit member 14 having an inlet end 16 and an outlet end 18 (FIG. 2) and a central passageway 20 extending therebetween. The inlet end 16 of the conduit member 14 faces the aerosol to be sampled. The outlet end 18 of the conduit member is connected to a return flow control valve 22 in the flow system 12, which is described in more detail below.

The conduit member 14 is formed of thin, gas-permeable material. This material is preferably formed of sintered, stainless steel powder having 100 micrometer pore diameters. Suitable material for this purpose is manufactured by Mott Metallurgical Corp., Farmington, Conn. Other gas-permeable materials may be used for all, or a portion of, the conduit member. For example, a tube formed of permeable polyetetrafluoroethylene would also be suitable. The material must be rigid enough to withstand gas pressure applied against it (as described more fully below) without collapsing.

The conduit member 14 is surrounded by a concentrically disposed tubular housing 26. One end of the housing 26 is contoured inwardly to join the inlet end 16 of the conduit member 14 and define the leading end 28 of the virtual impactor 10. The other end of the housing branches away from the conduit member and is connected to a hereinafter-described operating gas control valve 30 in the flow system 12. The space between the conduit member 14 and the housing 26 defines a chamber 32.

The virtual impactor formed in accordance with this invention employs an operating gas for both controlling aerosol particle entry into the passageway 20 of the conduit member 14, and for transpoting those particles through the conduit member to a region where they can be collected or analyzed in situ.

Turning now to the operating gas flow system shown in FIG. 2, that system comprises a vacuum and pressure pump 34 interconnected between the return flow control valve 22 and the operating gas control valve 30. The pump is connected and arranged to apply suction to the outlet end 18 of the conduit member and to pressurize the chamber 32 with operating gas drawn from a suitable source 36. The operating gas can be air or an inert gas such as helium, nitrogen or argon. The inert gases are desirable for situations where the analytical instruments employed require the absence of oxygen. The operating gas can also be a mixture containing reagents such as ozone, chlorine or hydrogen.

An analysis/collection region 38 is incorporated into the system adjacent to the outlet end 18 of the conduit member 14 and upstream of the return flow control valve 22. Separated particles are transported to this region where they are available for analysis and/or collection. This region includes instruments suitable for collecting or measuring the characteristics of the particular particles under study. For example, when liquid droplets are sampled, a nephelometer, a hygrometer and a condensation nuclei counter are included, as are filtering devices, mass flow meters, temperature gauges, etc.

An operating gas treatment subsystem 40 is incorporated into the flow system between the pump 34 and the operating gas control valve 30. This subsystem includes filters and scrubbers for removing impurities in the operating gas, which is supplied to the pump 34 from the operating gas source 36 and from the gas returned from the virtual impactor as described below. If the aerosol particles to be studied are liquid droplets, it has been pointed out that it is desirable in most cases to evaporate the liquid in order to measure the vapor of the solvent and liberate its solutes for separate collection and/or analysis. Thus a heater is included in the operating gas treatment subsystem 40 to heat the operating gas for the evaporation process.

The operating gas, the flow of which is symbolized by $F_1$ in the figures, is pumped through the treatment subsystem 40 and into the chamber 32 of the virtual impactor. The flow rate of the operating gas is controlled by the operating gas control valve 30. From the chamber 32, the operating gas passes through the permeable wall 24 of the conduit member and is bifurcated into opposing flow fractions, namely a transporting flow fraction, symbolized by $F_2$ in the figures, which is drawn by pump 34 back to the outlet end 18 of the conduit member through the analysis/collection region 38; and a counterflow fraction, symbolized by $F_3$ in the figures, which flows outwardly from the inlet end 16 of the conduit member. The transporting flow fraction $F_2$ is controlled by the return flow control valve 22, and as long as that flow rate is less than the initial operating gas flow rate $F_1$, there will always be a counterflow fraction $F_3$. Increasing or decreasing the transporting flow rate $F_3$ will correspondingly decrease or increase the rate of the counterflow fraction $F_3$. It is clear that if the transporting flow $F_2$ is adjusted to equal the operating gas flow $F_1$, then there will be no counterflow fraction $F_3$ effecting particle separation.

Separation of aerosol particles for analysis with a virtual impactor formed in accordance with this invention generally comprises two steps. Firstly, particles from the aerosol are directed into the inlet end 16 of the conduit member 14. These particles make up an aggregate sample having sizes (as quantified by their stop distances L) smaller than the minimum size of particle desired for collection and/or analysis (this latter size is known as the "cut size"). Secondly, the counterflow fraction $F_3$ of the operating gas is adjusted to expel particles from the passageway 20 that are smaller than the cut size.

For the initial separation of the aggregate sample of particles from the aerosol, the virtual impactor is moved relative to the aerosol in order to create an impaction velocity $V_i$. The leading end 28 of the virtual impactor is contoured to direct the flow of the aerosol around it. For a substantially hemispherically-shaped leading end, the minimum radius of curvature $r_c$ of the aerosol streamlines 29 flow around the leading end 28 of the impactor is approximately equal to the radius of the leading end of the impactor. Thus, for a virtual impactor having a radius of 1 centimeter at its leading end, particles having a stop distance L greater than 1 centimeter (i.e., a Stokes number greater than 1) will deviate from the aerosol flow and be directed into the passageway 20 of the conduit member 14. For example, for an impaction velocity of 100 meters per second, liquid droplets having a radius of 3.0 micrometers have a stop distance of approximately 0.6 centimeter. Thus, particles of this size or larger will enter the inlet end of the conduit member.

Once particles having Stokes numbers greater than 1 are directed into the passageway of the conduit member 14 they must completely traverse the counterflow fraction $F_3$ of the operating gas in order to reach the transporting flow fraction $F_2$ that will transport them to the analysis/collection region 38. The length $L_c$ of the counterflow fraction $F_3$ is the length between the point of division of transporting flow and counterflow fractions (i.e., the flow stagnation plane 42, FIG. 1) to the inlet end 16 of the conduit member. It is clear that particles must have a stop distance L at least as long as $L_c$ in order to reach the transporting flow fraction $F_2$. Assuming even distribution of the operating gas flow $F_1$ through the permeable wall 24 of the conduit member 14, and assuming that the portion of the wall 24 enclosed by the housing 26 has a constant length X, then the length $L_c$ of the counterflow fraction of flow relative to the length of the permeable wall can be approximated by the ratio of the counterflow rate $F_3$ out of the virtual impactor to the return flow rate $F_2$, or in equation form:

$$L_c/X = F_3/F_1$$

$$L_c = (F_1 - F_2)/F_{19} \cdot X$$

From the above equation it is clear that by merely adjusting relative flow rates $F_1$ and/or $F_2$, the counterflow length $L_c$ can be changed. Accordingly, by changing the counterflow length $L_c$, the number of particles that can traverse that distance $L_c$ will correspondingly change. Therefore, particle sample cut sizes can be changed instantaneously by merely altering the flow rates $F_1, F_2$ without the need to alter the impaction velocity or the structure of the virtual impactor. These flow rates can be adjusted during a sampling operation.

The magnitude of the flow of the counterflow fraction $F_3$ through the length $L_c$ will also affect the cut size. That is, an increased counterflow rate over a given distance $L_c$ will increase the drag force on the particle, thus reduce its velocity relative to $F_3$. Therefore the particle's stop distance L will be reduced. If the stop distance L of the particle is so reduced that it cannot traverse the counterflow distance $L_c$, it will be expelled from the passageway 20 of the virtual impactor. For example, experimentation has revealed that a virtual impactor having a 0.61 centimeter inlet opening and a length X of 10 centimeters that was passed through an aerosol at 107 meters per second, liquid droplet aerosol particles having less than approximately 8 micrometer radii were expelled from the passageway by the counterflow fraction $F_3$ of the operating gas when the operating gas was supplied at 20 liters per minute and controlled to provide 6.1 liters per minute of counterflow over a length $L_c$ of 3 centimeters. It can be appreciated that under lab conditions and using a prepared coarse-particle aerosol, the virtual impactor formed in accordance with this invention can be readily calibrated by one of ordinary skill in the art in order to determine a suitable counterflow rate and distance $L_c$ for any given cut size, operating gas flow rate $F_1$ and impaction velocity.

The ideal value for the transporting flow rate $F_2$ of the operating gas will depend upon the flow rate needed by any of the collection devices or analytical instruments used to measure the properties of the aerosol particles. In any event, the use of a counterflow fraction $F_3$ will cause all of the aerosol gas to be diverted from the passageway 20 of the conduit members 14. Therefore there is no opportunity for small-inertia particles (i.e., particles smaller than the cut size) to pass into the collection/analysis region via an undiverted portion of aerosol flow.

The virtual impactor formed in accordance with this invention will concentrate the number of the aerosol particles for sampling, thereby converting dilute, substantially immeasurable aersols into concentrated aerosols that are readily measurable. For example, a virtual impactor having a 0.9 centimeter diameter inlet and operated with an impaction velocity of 100 meters per second will receive an inflow of 380 liters per minute of aerosol. If the transporting flow in that virtual impactor is 8.5 liters per minute, by simple mass conservation, the particles from the inflow volume will be concentrated within the return flow fraction $F_3$ by a factor of approximately 45 (i.e., 380/8.5). Thus, for example, if the number concentration of liquid droplets in an aerosol is 100 per cubic centimeter, the number concentration of particles entering the analysis/collection region will be approximately 4,500 per cubic centimeter (assuming no coagulation or fragmentation of particles in the virtual impactor). This concentration makes measurement of these particles substantially more sensitive and accurate.

As noted earlier, particles separated from an aerosol by a virtual impactor formed in accordance with this invention are transported to the analysis/collection region by the transporting flow fraction of the operating gas. Since the operating gas passes through the permeable portion of the conduit member 14, there is a radially inwardly directed portion of the flow near the inner surface 24 of the conduit member. This radial flow functions to prevent particle collisions against the inner surface as the particles are being transported to the analysis/collection region 38. Preferably, the housing 26 (hence, the radially inwardly directed flow of the operating gas) completely surrounds the permeable conduit member from the inlet end 16 to a point that is very near the analysis/collection region 38. Thus particles entrained within the transporting flow fraction $F_2$ of the operating gas will undergo substantially no losses or contamination prior to in situ analysis or collection.

Figure 3:
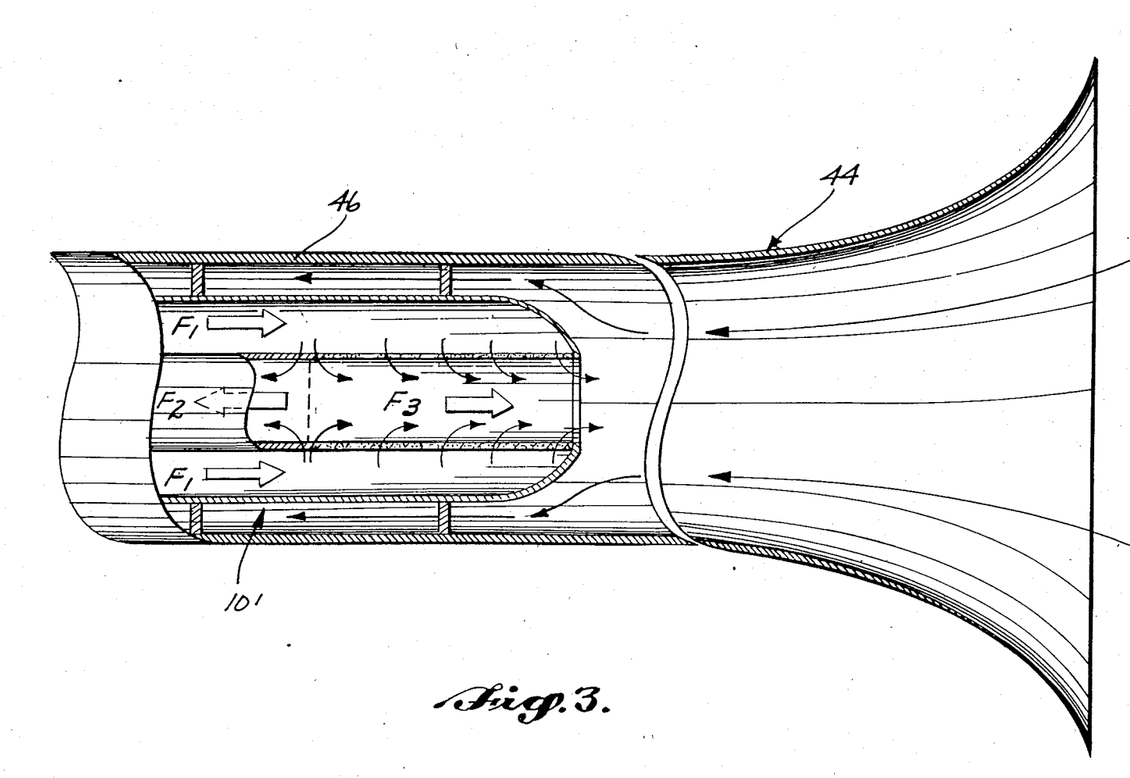
FIG. 3 is a schematic cross-sectional view of a virtual impactor formed in accordance with this invention in place within a venturi.
Figure 4:
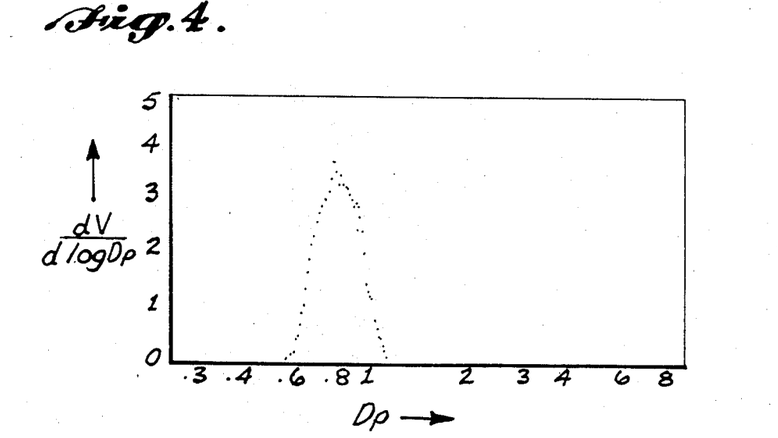
FIG. 4 is a diagram showing the size distribution of particles of a laboratory-produced aerosol that were separated and treated by a virtual impactor formed in accordance with this invention.

FIG. 3 shows a virtual impactor 10' that is structurally identical to the virtual impactor 10 described above adapted to reside within a venturi 44. The virtual impactor is fixed inside the throat 46 of the venturi. Space is provided between the virtual impactor and the wall of the venturi. The outlet of the venturi (not shown) is connected to a blower. This configuration permits the creation of an impaction velocity in the laboratory setting using a laboratory prepared aerosol. This configuration is especially useful for calibrating the impactor, or for ground-based sampling of aerosols such as high-humidity smog. Experiments were performed with this embodiment using a heated operating gas to evaporate a laboratory-prepared aerosol having liquid droplets as particles. Specifically, the venturi blower was adjusted to create an impaction velocity $V_i$ of 115 meters per second at the venturi throat 46. An aerosol having droplets between 5 and 40 micrometers in diameter was prepared using a $10^{-4}$ molar solution of ammonium sulfate. The operating gas of the virtual impactor was adjusted so that droplets smaller than approximately 16 micrometers in diameter were expelled by the counterflow fraction of the gas. Droplets larger than approximately 16 micrometers in diameter were evaporated by the heated transporting gas; the residual solute particles were then collected and measured. FIG. 4 shows the distribution of the residual particles; wherein Dp is the particle diameter in micrometers, and dV/d log Dp is the volume distribution function in terms of cubic micrometers per cubic centimeter.

A virtual impactor formed in accordance with this invention is not restricted to the tubular configuration described above. For example, with reference to the alternative embodiment of a vertical impactor 10" shown in FIG. 5, the conduit member 14" can be formed by a pair of flat parallel plates 15 joined at the edges and enclosed within a correspondingly shaped housing 26" to form a substantially slotted or oblong-shaped inlet opening 16". The plates 15 are formed of the same gas-permeable material described with respect to the embodiment shown in FIG. 1. This alternative embodiment would permit a relatively large volume of aerosol to be sampled or collected depending upon the length of the inlet end 16" of the conduit member 14"'. The operation of this embodiment is substantially the same as described with respect to the tubular shaped virtual impactor.

It is contemplated that the virtual impactor formed in accordance with this invention is applicable for separation of many types of aerosol particles. For example, airborne microorganisms, pollens, etc. having sufficient stop distances could be collected for analysis with this device. Furthermore, the use of a virtual impactor formed in accordance with this invention is not necessarily limited to sampling of aerosol particles. For example, it is also contemplated that such a virtual impactor could be readily adapted for use in processing certain products. For example, any liquid or semisolid solution of matter (coffee, radioactive material, pharmaceutical mixtures, etc.) that is amenable to conventional atomizing spray processes could be directed through the virtual impactor for separation and dehydration when the operating gas is sufficiently heated. Besides dehydration, chemical treatments can be applied to the separated particles, such as disinfection through use of any suitable oxidizing agent (such as chlorine gas) as the operating gas of the virtual impactor. Thus, while the invention has been described with reference to preferred embodiments, it is to be clearly understood by those skilled in the art that the invention is not limited thereto. Rather, the scope of the invention is to be interpreted only in conjunction with the appended claims.

The embodiments of the invention in which an exclusive property or privilege is claimed are defined as follows:

1. A device for separating particles from an aerosol where one of the device and the aerosol is in motion relative to the other and for transporting the separated particles, comprising:
   (a) a conduit member having an inlet end and an outlet end and defining a substantially enclosed passageway between its inlet and its outlet end, at least a portion of the conduit member that defines the passageway being gas-permeable, the passageway being adapted to receive at least a portion of the aerosol's particles through the inlet end as a result of the relative motion of the device and the aerosol; and
   (b) operating flow means associated with the conduit member for directing a gas through the gas-permeable portion of the conduit member and into the passageway, wherein a first fraction of the gas that is directed into the passageway exits the conduit member through the inlet end thereof, and wherein a second fraction of the gas that is directed into the passageway exits the conduit member through the outlet end thereof, a flow rate of the first fraction of the gas being adjustable to prevent passage through the passageway of some of the portion of the aerosol's particles, wherein aerosol particles received in the inlet end of the conduit member and not prevented from passing through the passageway by the first fraction of the gas are transported by the second fraction of the gas to the outlet end of the conduit member.

2. The device of claim 1, wherein the operating flow means includes a housing surrounding the conduit member, the housing being configured to define a chamber between the conduit member and the housing; and wherein the operating flow means is constructed so that the chamber is pressurized with the gas that is directed through the permeable portion of the conduit member into the passageway.

3. The device of claim 2 wherein the conduit member is substantially tubular and wherein the housing is substantially tubular.

4. The device of claim 2 wherein the inlet end of the conduit member is substantially oblong in cross section.

5. The device of claim 1 wherein substantially all of the conduit member is gas-permeable.

6. The device of claim 1 further including gas treatment means for filtering, scrubbing, and heating the gas that is directed into the passageway of the conduit member.

7. The device of claim 6 wherein the gas treatment means includes gas cleaning means for cleaning the gas, and heating means for heating the gas.

8. A device for separating particles from an aerosol where one of the device and the aerosol is in motion relative to the other comprising:
   (a) a conduit member having an inlet end and an outlet end and defining a substantially enclosed passageway between its inlet end and its outlet end, the passageway being adapted to receive at least a portion of the aerosol through the inlet end as a result of the relative motion of the device and the aerosol, at least a portion of the conduit member defining the passageway being gas-permeable;
   (b) flow means associated with the conduit member for supplying gas through the gas-permeable portion of the conduit member and into the passageway, and for drawing gas from the passageway through the outlet end of the conduit member; and
   (c) flow control means operatively associated with the flow means for controlling flow of the gas supplied to and drawn from the passageway in a manner that the gas that is supplied into the passageway is divided into a transporting flow fraction that is drawn from the outlet end and a counterflow fraction that exits through the inlet end and that forces a portion of the aerosol particles from the inlet end, whereby aerosol particles that are received within the passageway but not forced therefrom by the counterflow fraction are transported to the outlet end of the conduit member by the transporting flow fraction.

9. The device of claim 8 wherein the flow control means includes supply/return flow means for selectively varying the flow rates of the gas supplied through the passageway and the transporting flow fraction, the device being configured so that when the flow of the gas supplied to the passageway exceeds the transporting flow fraction the excess amount of supplied gas flow will exit the passageway as the counterflow fraction, the magnitude of the counterflow fraction thereby being adjustable by the supply/return flow means.

10. The device of claim 8, wherein the flow means includes a housing surrounding the conduit member, the housing being configured to define a chamber between the conduit member and the housing; the flow means and chamber being configured so that the gas is forced from the chamber into the passageway into the passageway through the permeable portion of the conduit member.

11. The device of claim 10 wherein the conduit member is substantially tubular; and wherein the housing is substantially tubular.

12. The device of claim 10 wherein the inlet end of the conduit member is substantially oblong in cross section.

13. A method for separating particles from an aerosol and transporting those separated particles through a conduit member that defines an interior passageway having an inlet and an outlet, wherein at least a portion of the conduit member is gas-permeable, the method comprising the steps of:
   (a) creating relative movement between the conduit member and the aerosol so that at least a portion of the aerosol is directed toward the inlet of the passageway of the conduit member;
   (b) directing an operating gas through the gas-permeable portion of the conduit member;
   (c) drawing a fraction of the gas that was directed through the gas-permeable portion of the conduit member out of the outlet of the passageway, whereby the remaining fraction of the gas exits the inlet of the passageway; and
   (d) controlling the flow of the operating gas so that the fraction of the gas that exits the inlet of the passageway forces a portion of the aerosol particles therefrom and so that the fraction of the gas that is drawn out of the outlet of the passageway transports the remaining particles in the passageway out of the passageway outlet.

14. The method of claim 13 including the substep of heating and cleaning the operating gas before directing it through the gas-permeable portion of the conduit member.

15. The method of claim 13, wherein the operating gas is a reagent.

16. The method of claim 13, wherein the operating gas is an inert gas.

* * * * *

UNITED STATES PATENT AND TRADEMARK OFFICE
CERTIFICATE OF CORRECTION

PATENT NO. : 4,689,052
DATED : August 25, 1987
INVENTOR(S) : Ogren et al.

It is certified that error appears in the above-identified patent and that said Letters Patent is hereby corrected as shown below:

Column 2, Line 48, "stolutes" should be --solutes--

Column 4, Lines 51 & 52, "polyetetrafluoroethylene" should be --polytetrafluoroethylene--

Column 4, line 68, "transpoting" should be --transporting--

Column 6, Line 53, "$F_{19}$" should be --$F_1$--

Column 8, Line 37, "vertical" should be --virtual--

Column 10, Lines 39 & 40, delete "into the passageway" (second occurrence)

Signed and Sealed this

Nineteenth Day of January, 1988

Attest:

DONALD J. QUIGG

*Attesting Officer*    *Commissioner of Patents and Trademarks*

UNITED STATES PATENT AND TRADEMARK OFFICE
CERTIFICATE OF CORRECTION

PATENT NO. : 4,689,052

DATED : August 25, 1987

INVENTOR(S) : Ogren et al.

It is certified that error appears in the above-identified patent and that said Letters Patent is hereby corrected as shown below:

Title page, field [75], line 2     "Heinzenberg" should be --Heintzenberg--

Title page, field [75], line 3     "Robert L." should be --Robert J.--

Signed and Sealed this

Twenty-third Day of February, 1988

Attest:

DONALD J. QUIGG

Attesting Officer          Commissioner of Patents and Trademarks